United States Patent [19]
Brooks, Jr.

[11] Patent Number: 5,896,088
[45] Date of Patent: Apr. 20, 1999

[54] INCIPIENT FIRE DETECTION SYSTEM

[75] Inventor: William K. Brooks, Jr., Newport News, Va.

[73] Assignee: Southeastern Univ. Research Assn., Newport News, Va.

[21] Appl. No.: 08/840,745

[22] Filed: Apr. 16, 1997

[51] Int. Cl.$^6$ .................................... G08B 21/00
[52] U.S. Cl. .................. 340/632; 340/522; 340/578; 250/343; 250/338.5
[58] Field of Search ................... 340/632, 640, 340/628, 627, 578, 630, 629, 522, 286.05, 577, 572; 250/341.8, 338.5, 343

[56] References Cited

U.S. PATENT DOCUMENTS

| | | | |
|---|---|---|---|
| 3,922,656 | 11/1975 | Horvath et al. | 340/522 |
| 4,583,597 | 4/1986 | Spector et al. | 340/578 |
| 4,823,009 | 4/1989 | Biemann et al. | 250/341.8 |
| 4,823,114 | 4/1989 | Gotisar | 340/578 |
| 4,843,243 | 6/1989 | Biemann et al. | 250/341.8 |
| 5,451,787 | 9/1995 | Taylor | 250/338.5 |
| 5,554,785 | 9/1996 | Trapasso et al. | 560/201 |

*Primary Examiner*—Jeffery A. Hofsass
*Assistant Examiner*—Davetta Woods

[57] ABSTRACT

A method and apparatus for an incipient fire detection system that receives gaseous samples and measures the light absorption spectrum of the mixture of gases evolving from heated combustibles includes a detector for receiving gaseous samples and subjecting the samples to spectroscopy and determining wavelengths of absorption of the gaseous samples. The wavelengths of absorption of the gaseous samples are compared to predetermined absorption wavelengths. A warning signal is generated whenever the wavelengths of absorption of the gaseous samples correspond to the predetermined absorption wavelengths. The method includes receiving gaseous samples, subjecting the samples to light spectroscopy, determining wavelengths of absorption of the gaseous samples, comparing the wavelengths of absorption of the gaseous samples to predetermined absorption wavelengths and generating a warning signal whenever the wavelengths of absorption of the gaseous samples correspond to the predetermined absorption wavelengths. In an alternate embodiment, the apparatus includes a series of channels fluidically connected to a plurality of remote locations. A pump is connected to the channels for drawing gaseous samples into the channels. A detector is connected to the channels for receiving the drawn gaseous samples and subjecting the samples to spectroscopy. The wavelengths of absorption are determined and compared to predetermined absorption wavelengths is provided. A warning signal is generated whenever the wavelengths correspond.

14 Claims, 4 Drawing Sheets

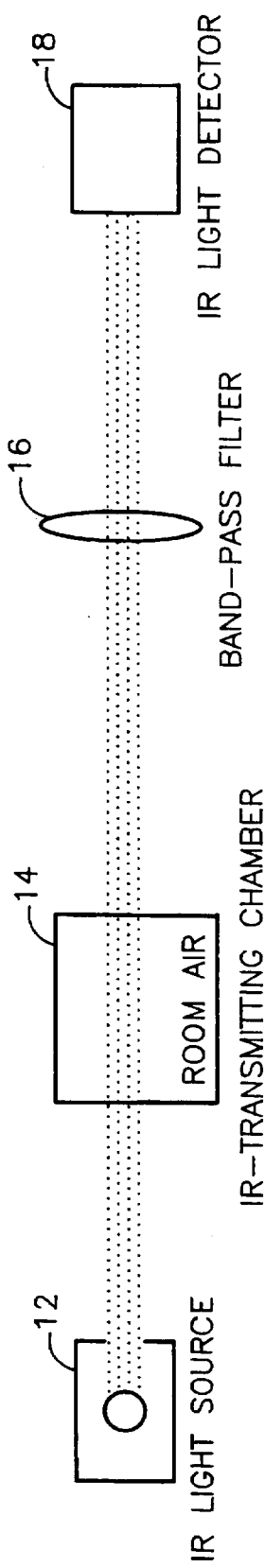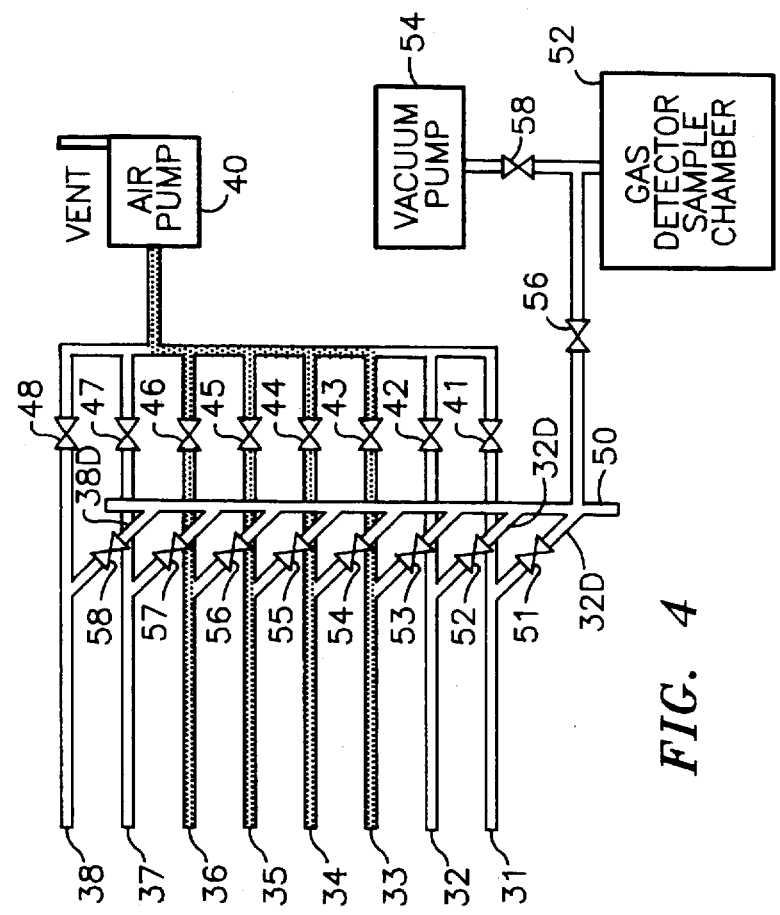
FIG. 1
FIG. 4

INCIPIENT FIRE DETECTION SYSTEM

BACKGROUND OF THE INVENTION

1. Field of the Invention

The present invention pertains to fire detection systems and more particularly to fire detection systems that are capable of detecting conditions that are indicative of imminent combustion.

2. Related Prior Art

Fire protection regulations in the United States focus on two basic issues, protection of people and protection of buildings. The fire protection industry, who helps form the regulations, also focuses on these two issues with the primary focus on protection of people. In the secondary issue of protecting buildings, the protection of the contents of the building has been traditionally secondary and not as high a priority as the building. It is assumed that the contents of the building are protected by conventional fire systems. Since the value of the contents of a building is usually much less than that of the building, fire insurance coverage is relied upon as the most cost effective way to deal with this problem.

In most situations the focus on building safety is appropriate. However, in some instances, building protection is not where emphasis should be placed. Exceptions to the building first type of focus include high tech facilities where a high concentration of extremely expensive equipment is located or where service interruption is highly undesirable, such as a key defense facility. In general, these facilities are unmanned and personnel protection is not a consideration. Although personnel protection is always the highest priority, in the listed exceptional situations the integrity and operation of the building contents become more important than the building. In addition, this type of equipment is often significantly more vulnerable to fire damage from even small sized fires.

A variety of approaches have been used to solve this problem. Incipient fire detection systems of varying levels of sophistication have been built by a number of facilities. The commercial VESDA (Very Early Smoke Detection Apparatus) system is an example of a smoke/aerosol based early warning system which is widely used. In a different approach, Fermi National Laboratory has designed and currently operates an early warning system based on an evolved gas signature in order to protect the CDF detector.

Incipient detection systems of this type are completely site specific. An analysis of the likely ignition scenarios and of the combustible fuels in a given location is performed first. When the most likely fuel is identified, a literature search is performed to try to determine what gasses are given off by this material when it is heated. Typically there are several gasses that are given off and detectors for these specific gases are obtained. The detectors are then either mounted in the area of interest or mounted at the output end of a gas sampling system which samples the areas of interest. Detection of these gases in coincidence triggers a fire alarm.

Prior art systems have several weaknesses, some of which are listed as follows.

Initially, the prior art systems are completely specific to one fuel. If a second source of fuel is present and heated or ignited, the system could be potentially blind to this fuel if the gases given off are different than the ones for which the system is designed. Upgrading the system to detect a new set of gases will increase the number of gas detectors required. In a sequential gas sampling system, this may affect the sampling time at each point depending on the time response of the new detectors. The overall cost of the revised system increases a new gas detectors are added and maintained.

Another weakness is that the transport efficiency of some gases through sampling systems, for example, HCl gas, is known to depend strongly on the sampling tube type and length. For a system with two different tube lengths the gas mixture from a given combustible may be quite different coming from one monitored area than from another.

The precise species and relative concentrations of gases given off and transported through the sampling system depends on the rate of heating and other environmental effects such as humidity.

An additional weakness is that for a given combustible, the available literature may not include all the gases evolved when the material is heated, particularly when it is heated at different rates. Little or no information on unusual combustibles may be available. Therefore, a crucial signature of a fire precursor may be designed out of a system from the start.

Another weakness exists in the entire method. The entire method is predicated on the early apprehension of gases above their ambient concentrations. The time constants for existing electrochemical gas detectors and detectors employing optical filters are typically greater than the gas transit time through long sampling tubes in practical systems. The detector response time is therefore the main delay in any system employing sequential sampling of mote than a few locations, and the overall system delay grows with the number of sampling points.

In prior art systems the overall fire protection system cannot easily be packaged into a commercial product. The system built at one site is not likely to be optimal or adaptable to a different site, unless the combustible inventory and the spatial layout of the two systems are nearly identical. Each individual system is basically a large scale research project.

Examples of prior art systems are illustrated in the following U.S. Patents, all of which have one or more the foregoing deficiencies.

U.S. Pat. No. 5,519,382, titled "Mobile Fire Detector System", issued to Tim E. Pope et al., relates to a mobile fire detecting system that detects fire conditions st their incipient stage prior to the presence of visible smoke. This system contains an air sampling fire detector mounted to a cart supported by wheels. A tubular network in communication with the air sampling detector has a manifold enclosed by a box with four sensing hoses releaseably connected to the lateral outlets of the manifold and a telescoping mast supporting the manifold to position it at selectable heights. Four sampling heads are connected to the other ends of the sensing hoses and are peripherally spaced equally so that the maximum area is sampled for air to detect fire conditions.

U.S. Pat. No. 5,475,222, titled "Ruggedized Gas Detector", issued to John D. King, relates to a gas detector having two or more perforated concentric cylinders and having a concentric screen inside the innermost cylinder. A pair of perforated tubes are positioned inside the perforated screen, and an infrared light source is placed adjacent one end of one of the tubes and an infrared sensor is placed adjacent the other tube. A pair of inclined mirrors are positioned adjacent the respective other ends of the two tubes, and an optical light path is created from the IR source through a first tube, reflected by the mirrors to a return optical path through the second tube and ultimately to the IR sensor.

U.S. Pat. No. 4,264,209, titled "Gas Detector", issued to Arthur E. Brewster, relates to an apparatus for illuminating a gas or gas mixture and filtering the output thereof alternately with two filters. One filter has a passband at an absorption band of a gas to be detected. The other filter has a passband outside the absorption band.

U.S. Pat. No. 5,341,214, titled "NDIR Gas Analysis Using Spectral Ratioing Technique", issued to Jacob Y. Wong, relates to an instrument for determining the concentration of a particular gas that might be present in a sample using a waveguiding structure to serve both as an optical element and as a sample chamber. As an optical element, the waveguiding structure collects radiation from a black body source located at the entrance end of the waveguiding structure and conducts the radiation through the waveguiding structure, concentrating it on two infrared detectors mounted at the opposite end of the waveguiding structure. As a sample chamber, the waveguiding structure causes the radiation to undergo multiple reflections that result in the average path length being substantially greater than the physical length of the waveguiding structure. Each of the detectors has its own optical filter, and baffling assures that each detector responds only to radiation which has passed through its filter. One filter defines a spectral passband that coincides with the infrared absorption band of the gas to be measured. The other filter defines a non-absorbing or neutral passband. The electrical signals produced by the detectors are processed to provide a ratio, the value of which is related to the concentration of the particular gas to be detected.

SUMMARY OF THE INVENTION

The present invention is intended to obviate several weaknesses in the prior art systems. The light absorption spectrum is measured as a function of wavelength for the gases given off by heated materials. Gas samples are taken from the areas of interest. The light absorption spectrum of the gas samples is also measured as a function of wavelength. The two measurements are compared to determine whether the wavelength fingerprint of the gases given off by heated materials is present in the light absorption spectrum of the gas samples. A Fourier Transform Infrared (FTIR) Spectroscope is preferred as the device for measuring absorption spectrums. The technique used by the FTIR spectroscope measures infrared absorption of gases over a fairly wide range of wavelengths. The output can then be analyzed to determine what gases are present based on known absorption characteristics. The time constant of measurement is of the order of a few seconds or less. In a clean environment, the results of the measurement can be sensitive at the few hundred ppb level or better.

The operation of the present invention consists of interfacing a commercial FTIR spectroscope unit to a sequential sampling system connected to a variety of locations to be monitored. The system of the present invention is calibrated for each of the monitored areas. The calibration consists of heating samples of combustible materials located in each area and observing the wavelength spectrum measured by the FTIR unit. The heating may be performed at different rates and under different environmental conditions, such as varying humidity, and the results analyzed to determine the range of responses the system has to each combustible present under all conditions of interest. After calibration, the analysis of the gases drawn from each area monitored can look for the precise signature of the appropriate combustible. Measurable environmental variables can also be factored into the gas analysis, such as the humidity of the sample gas, which may affect transport rate of some gases.

BRIEF DESCRIPTION OF THE DRAWINGS

FIG. 1 is an illustration depicting an incipient fire detection system using light absorption.

FIG. 4 is a partial block diagram of an incipient fire detection system using an infrared gas detector during an initial sample gathering stage.

DESCRIPTION OF THE PREFERRED EMBODIMENT

Figure 2:
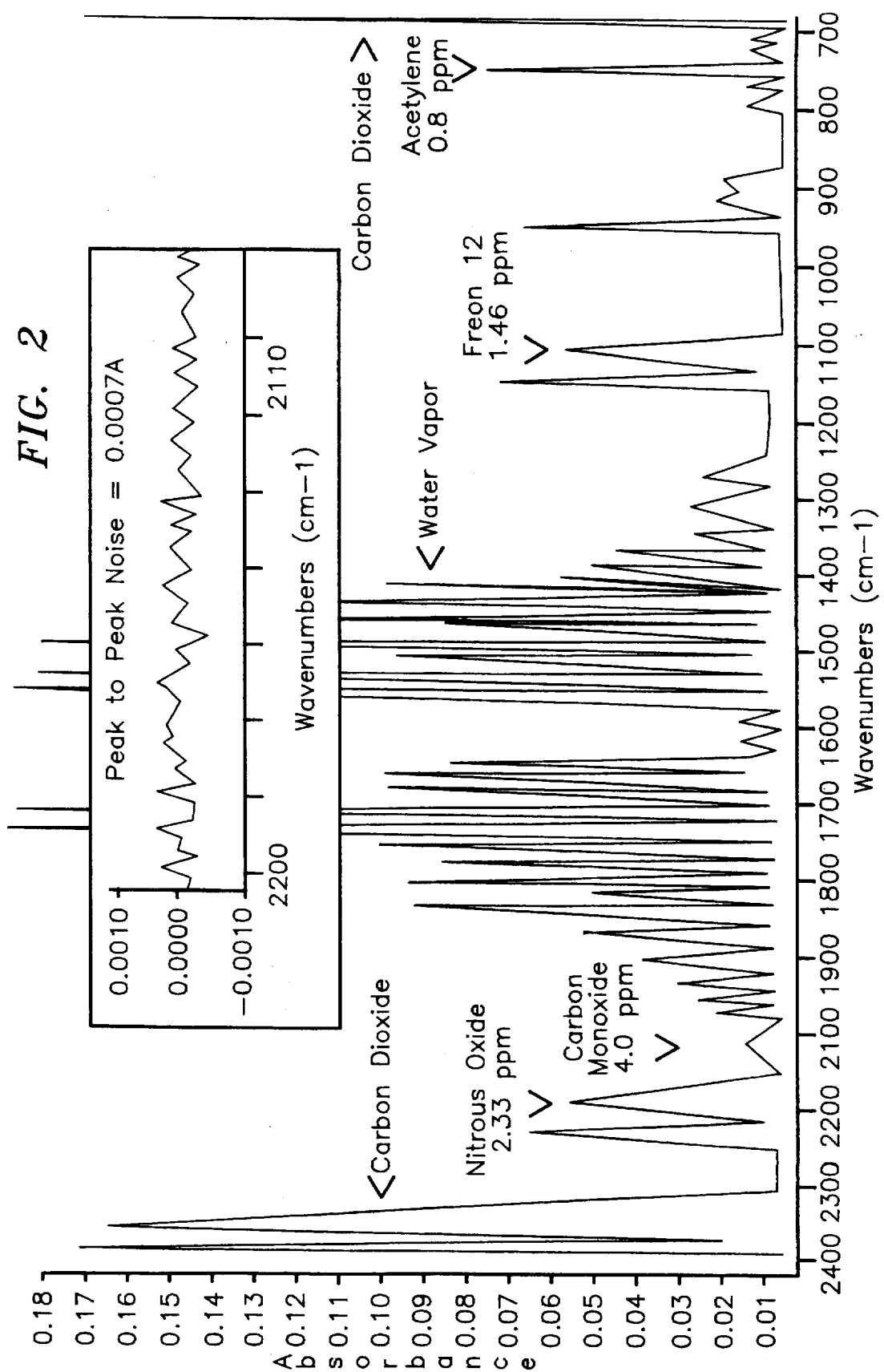
FIG. 2 is a graphical representation of an absorption spectrum for a group of gases.

As indicated previously, present day incipient fire detection systems have several deficiencies. These known systems are completely specific to one fuel. Transport efficiency of some gases through sampling systems, for example, HCl gas, is known to depend strongly on the sampling tube type and length. The precise species and relative concentrations of gases given off and transported through the sampling system depends on the rate of heating and other environmental effects such as humidity. For a given combustible, the available literature may not include all the gases evolved when the material is heated, particularly when it is heated at different rates. The entire method of known systems is predicated on the early apprehension of gases above their ambient concentrations. The overall fire protection system cannot easily be packaged into a commercial product. The system built at one site is not likely to be optimal or adaptable to a different site, unless the combustible inventory and the spatial layout of the two systems are nearly identical. Each individual system is basically a large scale research project.

In its simplest form, the method and apparatus of the present invention is illustrated in FIG. 1. An infrared light source 12 is used to generate an infrared light beam through an infrared transmitting chamber 14. In a preferred embodiment, chamber 14 is to have quartz windows for improved accuracy and avoidance of spurious readings due to other types of windows. Once the beam travels through chamber 14, it is passes through band pass filter 16 and is received by infrared light detector 18. In operation, chamber 14 contains an air sample of the room which is being monitored. This air sample is constantly being recycled to constantly monitor the air within the monitored area. The element of this system which provides specificity is band pass filter 16. In the following example, filter 16 is an optical device used in the isolation of carbon monoxide. Filter 16 filters out all the light except the light having a wavelength absorbed by carbon monoxide, which is a narrow wavelength range. If the filter is chosen so that only light which is absorbed by carbon monoxide is transmitted through the filter, then the output of infrared light detector 18 indicates the amount of carbon monoxide present. This embodiment makes use of wavelength specific light absorption to detect a pre-fire or fire condition.

For example, the gas for which the detector could be set is carbon monoxide. In an installation which contains items such as plastic cables, carbon monoxide is an appropriate choice. It is known that when most plastic cable jacketing gets hot, it emits carbon monoxide. When the jacket catches fire, it will continue to emit carbon monoxide. The normal atmospheric concentration of carbon monoxide is about one ppm. As the cable jacket becomes overheated in a somewhat enclosed area, the concentration of carbon monoxide in the air would rise above the normal atmospheric concentration. The detector can be set to sound an alarm when it detects a carbon monoxide concentration significantly greater than one part per million.

The present invention obviates all the foregoing problems by using a Fourier Transform Infrared Spectroscope as detector 18 to measure the light absorption spectrum of the samples and comparing the measured light absorption spectrum with known light absorption spectrum of gases given off by heated materials.

Basing an incipient fire detection system on the presence of carbon monoxide may prove unreliable and initiate false alarms under certain conditions. For example, in an area where gas operated vehicles operate routinely, carbon monoxide may be present in high enough quantities to trigger the alarm. A simple system based on the detection of carbon monoxide would continually produce false alarms. However, usually more than one kind of gas is given off by a specific heated combustible. Several systems similar to the one previously described could be used , where each separate system has a different type of band pass filter which selects wavenumbers corresponding to other gases. The presence of several gases in combination can be taken as a fingerprint foe a pre-fire or fire condition. The alarm can be sounded only if the specific combination of gases is seen in sufficient concentrations. The benefit of this approach is that the system can be calibrated to a given fuel, that is the incipient fire detection system can be made to be fuel specific.

Figure 3:
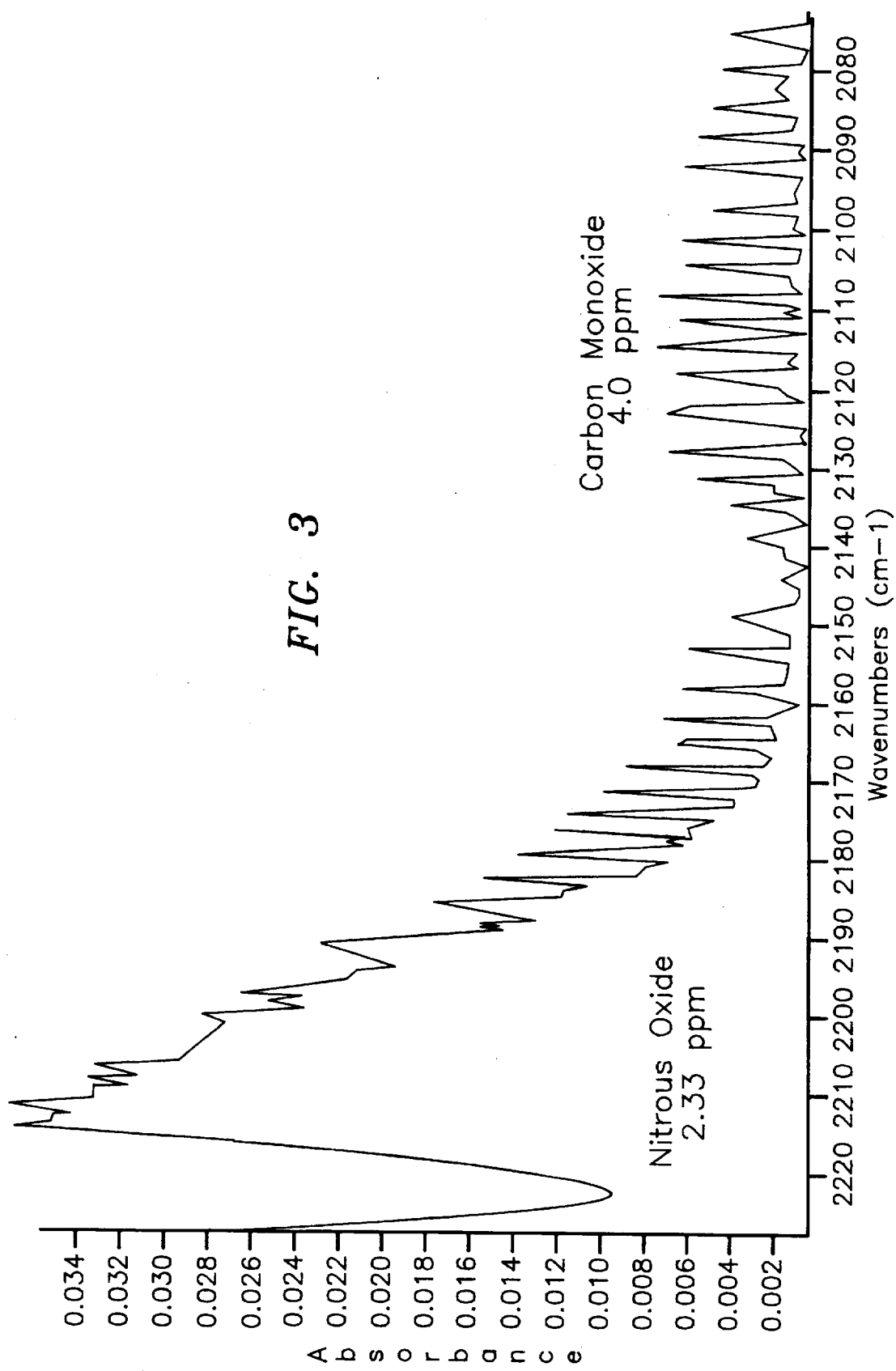
FIG. 3 is an enlarged graphical representation of a portion of FIG. 2.

FIG. 2 is a graph illustrating the wavenumbers of various wavelengths of light and the absorbance of several gases and water vapor at identified wavelengths. As can be seen, water vapor has a significant absorbance values from wavenumbers of about 1900 to about 1350. Essentially, no meaningful information can be obtained in the wavenumber range in an area where the humidity is very high. Fortunately, the most common indicators of incipient fires fall within the wavenumber range from about 2230 to about 2070 as illustrated in FIG. 3. It is in this range that absorption for carbon monoxide and nitrous oxide occur. These two gases are two of the most common gases emitted by present day man made materials when they burn.

Referring now to FIG. 4, an apparatus for incipient fire detection is illustrated in partial block form. Channel system 30 is illustrated as having channels 31–38 with their endpoints at various locations throughout an area to be monitored. Each channel 31–38 is connected to air pump 40 through valves 41–48, respectively. At a predetermined point, each valve 31–38 bifurcates and includes a passage 31D–38D, respectively, connected to manifold 50 through valves 51–58, respectively. Manifold 50 is connected to gas detector sample chamber 52 and to vacuum pump 54 through valve 56. Gas detector sample chamber 52 is connected to vacuum pump 54 through valve 58. In FIG. 4, the area connected to channel 33 is to be tested. Valves 43, 44, 45 and 46 are opened and gas samples are being drawn. At this time, valves 41, 42, 47 and 48 along with valves 51–58 are closed. Valve 56 is closed and valve 58 is open, allowing pump 54 to evacuate chamber 52.

Figure 5:
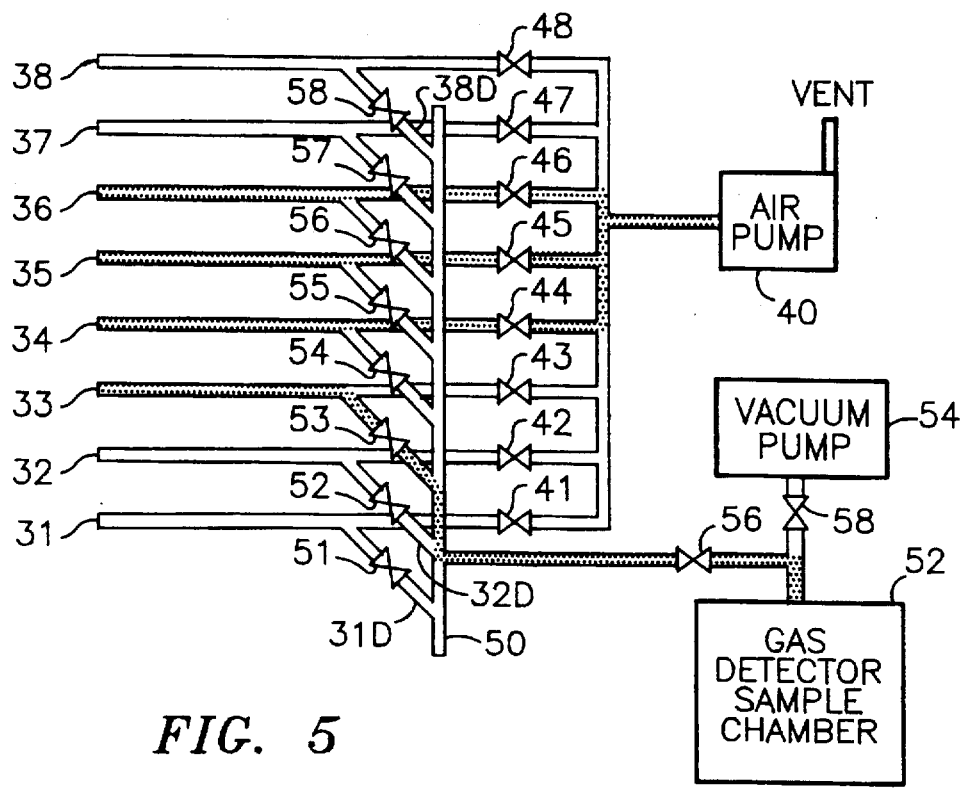
FIG. 5 is a partial block diagram of an incipient fire detection system using an infrared gas detector during a sample isolating stage.

In FIG. 5 a sample is being taken from channel 33. Valve 43 is closed and valve 53 is opened. Valve 58 is closed and valve 56 is opened. This allows the vacuum that has been drawn in sample chamber 52 to draw the gas sample from channel 33 to sample chamber 52 for analysis.

Figure 6:
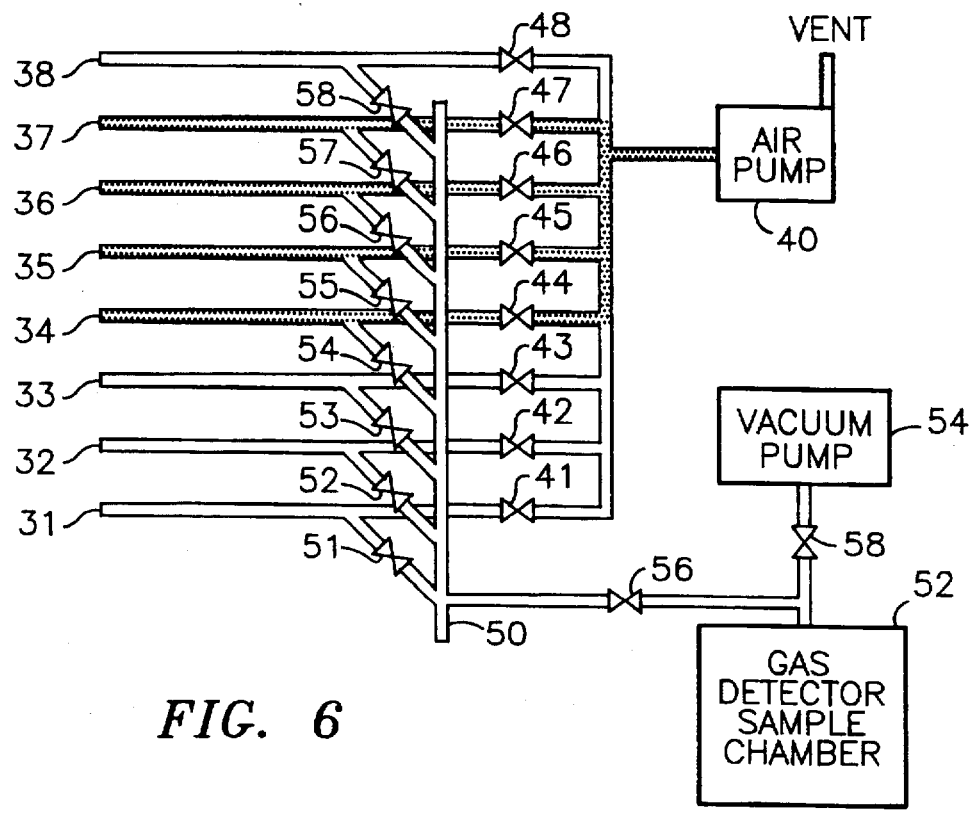
FIG. 6 is a partial block diagram of an incipient fire detection system using an infrared gas detector during a sample analysis stage.

FIG. 6 illustrates the operation of the system while the gas sample from channel 33 is being analyzed. At this time, valve 53 is closed, valve 56 is closed and valve 47 is opened. This allows a gas sample to be drawn into channel 37 for further sampling. In this manner, as soon as the sample from channel 33 has been analyzed, a new ample from the next channel can be drawn into chamber 52 without a delay necessitated by the time required to draw the sample from the remote location of the next channel end.

There are several gas detector technologies which use a wavelength based approach to identifying the gas of interest. Non dispersive infrared gas detectors, for example, typically use a sample of the gas of interest itself as an optical filter. Noise rejection and stabilization against signal drift are important considerations in designing a practical device to look for low concentrations. Low concentrations can be defined as in the few parts per million range (ppm). The time required to sample the gas can be thirty to ninety seconds for off the shelf detectors with a one ppm minimum sensitivity. A more flexible approach is taken in the preferred embodiment which uses a gas detector based on Fourier Transform Infra-Red (FTIR) spectroscopy. The FTIR gas detectors can find a combination of gases in a single measurement. Reconfiguring a given detector to look for a different set of gases is a trivial software change, in contrast to the simple system described in conjunction with FIG. 1, where changing band pass filters is the only way to reconfigure for a different gas mixture. For more than a few gases the FTIR approach is also more cost effective. The FTIR approach also can offer very high sensitivity and rapid measurements, depending on its configuration. In broad terms, FTIR detectors produce a plot of the amount of light absorbed as a function of wavelength from a given air sample. The pattern of light absorption as a function of wavelength of a given gas is caused directly by the molecular structure of the gas. Therefore, different gases have different patterns, and these patterns can be searched for in the sample of room air using well known sophisticated mathematical procedures.

The hardware used by the FTIR gas detector to produce the absorption spectrum is well known in the art and is called a Michaelson interferometer. This device produces an intensity pattern as a function of mirror position. The intensity as a function of position can be transformed into the intensity as a function of wavelength by the mathematical procedure known as the Fourier transform, an infinite mathematical series.

There are several advantages of the FTIR gas detector. Multiple gases can be detected and the selection of detected gases can easily be changed. This feature permits calibration in place in the sense that whatever conditions affect the gas evolution from the fuel can be studied and incorporated into the system. Meaningful measurements can be made in just a few seconds, which is important in an early warning system. This makes it feasible to connect this detector to a gas sampling system without much of a time penalty. The stability characteristics of these instruments are very good and can operate continuously for days or weeks without maintenance.

While the method and apparatus of the present invention is fuel specific, the protection from a new type of fuel only requires that a different wavelength profile be calibrated rather than increasing the number of types of gas detectors. As long as the gases absorb in the wavelength range to which the detector is sensitive, they can be accommodated by the system.

The transport efficiency of the system for a given gas will be directly calibrated into the response of the instrument for a given area. Thus, if the tubing length for one area permits transport of one gas species, but the tubing length for a different area does not, the calibrated wavelength profile for each of the two areas will reflect this fact.

If the mixture of gases evolved from a combustible depends on factors such as rate of heating or other environmental variables, these variations can be studied in the calibration procedure and taken into account in the analysis.

The current information available in the world's database on a given combustible does not limit the sensitivity of the system nor affect its design. This is because all gases absorbing, for example, in the infrared spectrum, will be seen in the calibration procedure, even if they have never been identified in the literature as evolving from a particular combustible.

The time constant for this type of measurement can be short enough that the system delay is likely to be due to the transport delay of the gases from the monitored area to the FTIR unit, and not due to the measurement time. This means that expanding the number of monitored points does not increase the time delay of the system for a reasonable number of points.

The system embodying the method and apparatus of the present invention could be sold commercially. Adaptation of a system from one site to another is far easier, since the variations in gas species evolves and environmental conditions can be taken into account in the calibration procedure.

Although the gases given off by heated materials tend to absorb mainly in the infrared, the same principle could be applied with absorption in the TV or other wavelength range. In the preferred embodiment an FTIR unit is used for clarity, however, the principle applies to any instrument measuring a wavelength spectrum.

A range of possibilities have been described which make use of the principle of detection of fire or pre-fire conditions by wavelength specific light absorption. A simple, low cost system can be constructed which has limited sensitivity, but is competitive with commercial smoke detectors. In a alternate embodiment, a high sensitivity, flexible system has been described which provides an effective and reliable first alert alarm system. While there has been illustrated and described a particular embodiment of the present invention, it will be appreciated that numerous changes and modifications will occur to those skilled in the art, and it is intended in the appended claims to cover all those changes and modifications which fall within the true spirit and scope of the present invention.

I claim:

1. An apparatus for detecting incipient fires comprising:
   detection device for receiving gaseous samples from an area to be monitored subjecting said samples to spectroscopy and determining wavelengths of absorption of said gaseous samples;
   a source of absorption wavelengths of gases from products representing an area to be monitored evolving from heated combustibles prior to such combustible creating a fire so as to provide predetermined absorption wavelengths;
   a mechanism for comparing said wavelengths of absorption of said gaseous samples from an area to be monitored to said predetermined absorption wavelength that represent incipient combustion; and
   an alarm device for generating a warning signal of incipient combustion whenever said wavelengths of absorption of said gaseous samples from an area to be monitored correspond to said predetermined absorption wavelengths.

2. The apparatus according to claim 1 wherein said detection device includes a device for generating light wavelengths in the infrared range.

3. The apparatus according to claim 1 wherein said detector means includes a Fourier Transform Infrared detector.

4. The apparatus according to claim 1 wherein a light absorption spectrum of a mixture of gases include absorption wavelengths of carbon monoxide.

5. A method for detecting incipient fires comprising:
   receiving gaseous samples from an area to be monitored;
   subjecting said samples to light spectroscopy;
   determining wavelengths of absorption of said gaseous samples;
   providing predetermined wavelengths of absorption of representative heated combustible in said area prior to said combustibles creating a fire to furnish predetermined absorption wavelengths;
   comparing said wavelengths of absorption of said gaseous samples to said predetermined absorption wavelengths that represent incipient combustion; and
   generating a warning signal of incipient combustion whenever said wavelengths of absorption of said gaseous samples correspond to said predetermined absorption wavelengths.

6. The method according to claim 5 wherein said subjecting said samples to light spectroscopy includes generating light wavelengths in the infrared range.

7. The method according to claim 5 wherein said determining wavelengths of absorption includes providing a Fourier Transform Infrared detector.

8. The method according to claim 5 wherein said comparing wavelengths of absorption to predetermined wavelengths includes correlating said wavelengths of absorption to absorption wavelengths of carbon monoxide.

9. A method for detecting incipient fires comprising:
   receiving gaseous samples from an area to be monitored;
   subjecting said samples to light spectroscopy by generating light wavelengths in the infrared range;
   determining wavelengths of absorption of said gaseous samples by providing a Fourier Transform Infrared detector;
   providing predetermined wavelengths of absorption of representative heated combustibles in said area prior to said combustibles creating a fire to furnish predetermined absorption wavelengths;
   comparing said wavelengths of absorption of said gaseous samples from said area to predetermined absorption wavelengths representing gases emitted during incipient combustion by correlating said wavelengths of absorption to absorption wavelengths of carbon monoxide; and
   generating a warning signal whenever said wavelengths of absorption of s aid gaseous samples correspond to said predetermined absorption wavelengths.

10. An apparatus for detecting incipient fires comprising:
   channel system fluidically connected to a plurality of remote locations to be monitored for detecting incipient fires;
   pumping device connected to said channel means for drawing gaseous samples into said channel means;
   detector connected to s aid channel means for receiving said drawn gaseous samples and subjecting said samples to spectroscopy and determining wavelengths of absorption of said gaseous samples;
   a source of predetermined absorption wavelengths representing heated combustibles from said remote locations prior to said heated combustibles creating a fire;

comparator for comparing said wavelengths of absorption of said gaseous samples to predetermined absorption wavelengths; and alarm for generating a warning signal whenever said wavelengths of absorption of said gaseous samples correspond to said predetermined absorption wavelengths.

11. The apparatus according to claim 10 wherein said channel system includes a valve network for selectively closing and opening fluid communication with each of said plurality of remote locations.

12. The apparatus according to claim 10 wherein said detector includes a source for generating light wavelengths in the infrared range.

13. The apparatus according to claim 10 wherein said detector includes a Fourier Transform Infrared detector.

14. The apparatus according to claim 12 wherein a light absorption spectrum of a mixture of gases include absorption wavelengths of carbon monoxide.

* * * * *